Figure 1:
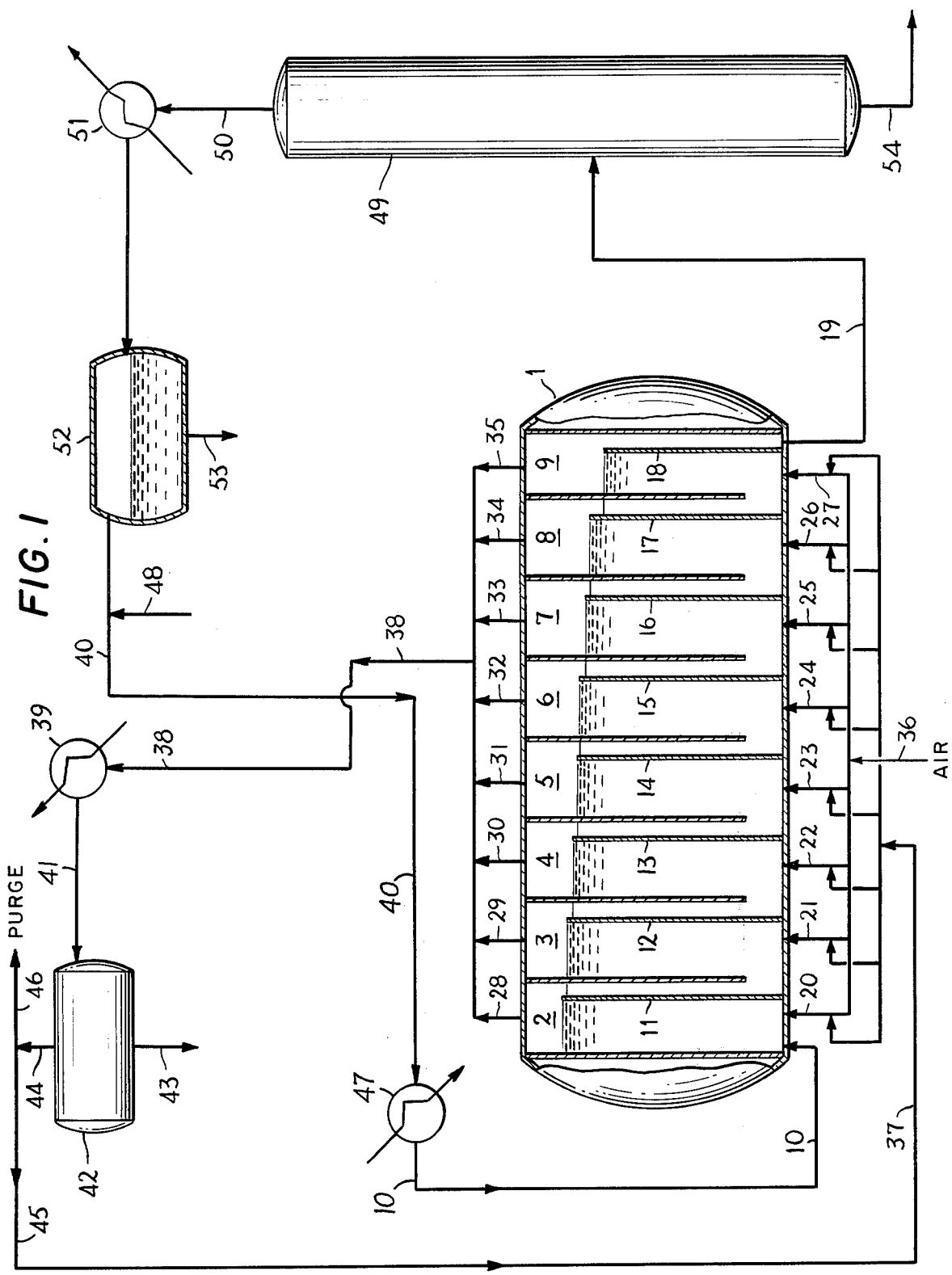

United States Patent [19]

Schmidt

[11] 4,066,706
[45] Jan. 3, 1978

[54] PREPARATION OF ETHYLBENZENE HYDROPEROXIDE

[75] Inventor: John P. Schmidt, Princeton, N.J.

[73] Assignee: Halcon International, Inc., New York, N.Y.

[21] Appl. No.: 569,734

[22] Filed: Apr. 21, 1975

[51] Int. Cl.² ............................................. C07C 179/02
[52] U.S. Cl. ................................................. 260/610 B
[58] Field of Search ......................... 260/610 B, 610 A

[56] References Cited

U.S. PATENT DOCUMENTS

| | | | |
|---|---|---|---|
| 2,637,772 | 3/1953 | Armstrong | 260/610 B |
| 3,351,635 | 11/1967 | Kollor | 260/610 B |
| 3,459,810 | 8/1969 | Choo | 260/610 B |

Primary Examiner—James O. Thomas, Jr.
Assistant Examiner—W. B. Lone
Attorney, Agent, or Firm—William C. Long; Riggs T. Stewart; David Dick

[57] ABSTRACT

The present invention is concerned with an improved process for the molecular oxygen oxidation of ethylbenzene in the liquid phase to ethylbenzene hydroperoxide. The improved process is particularly concerned with carrying out the oxidation in a series of separate oxidation zones at substantially constant pressure with the temperature being progressively reduced from zone to zone in the liquid phase, the temperature reduction and control being accomplished by recycle of inert gases.

5 Claims, 2 Drawing Figures

U.S. Patent  Jan. 3, 1978  Sheet 1 of 2  4,066,706

PREPARATION OF ETHYLBENZENE HYDROPEROXIDE

This invention relates to improvements in the production of ethylbenzene hydroperoxide by the oxidation of ethylbenzene.

Ethylbenzene hydroperoxide (alpha phenyl ethyl hydroperoxide) has found important uses in various chemical processes. For example, ethylbenzene hydroperoxide has been found to be an important reactant in the epoxidation of propylene to form propylene oxide. Illustrative is U.S. Pat. No. 3,351,635. It is, of course, known in the art to oxidize ethylbenzene to ethylbenzene hydroperoxide with molecular oxygen. Illustrative of recent improvements in this technology are U.S. Pat. Nos. 3,459,810 and 3,475,498 which describe preferred methods for improving the selectivity and efficiency of ethylbenzene oxidation to ethylbenzene hydroperoxide.

As taught in the above-mentioned U.S. Pat. No. 3,459,810, in the oxidation of ethylbenzene to ethylbenzene hydroperoxide it is of significant advantage to carry out the oxidation at progressively decreasing temperatures. Specifically, in a preferred continuous system employing a plurality of separate oxidation zones, it is preferred that the temperature be progressively reduced from zone to zone in the direction of liquid flow.

An obvious method of accomplishing the necessary temperature control is to adjust the pressure in each of the zones appropriately to provide for operation in the zone at the desired temperature level. However, it is difficult and expensive to provide appropriate means for controlling the reaction temperature by maintaining the zones at different pressures.

An alternative method of temperature control is to provide cooling coils or similar heat-transfer surfaces in each zone whereby the temperature therein can be regulated. Such procedures have, however, disadvantages in the high cost of the necessary apparatus and equipment. An additional disadvantage is the low energy efficiency of this method, since the heat removed from the lower temperature zones is generally available only at such a low temperature as to preclude utilization and is therefore wasted. Even if recovered, this heat is available at an insufficient temperature level to be utilized for preheating liquid feed to the first (high temperature) reaction zone; consequently there is a substantial loss of useful energy.

It is an object of the present invention to provide an improved method for the oxidation of ethylbenzene to ethylbenzene hydroperoxide wherein the desired temperature control can be achieved in a novel and effective manner.

In accordance with the present invention, ethylbenzene is continuously oxidized with molecular oxygen in the liquid phase in a series of separate agitated oxidation zones, maintained at substantially the same pressure, e.g., by use of a common vapor withdrawal system, while the temperature in the series of oxidation zones is decreased in the direction of liquid flow, i.e., from an upstream portion to a downstream portion, the temperature being controlled and regulated in each of the oxidation zones by the introduction of recycled inert gases which exert a cooling action by vaporizing ethylbenzene.

Surprisingly, higher selectivities are obtained when the reaction is carried out by the process of this invention than those obtained by conventional processing methods wherein temperature control is achieved by cooling through heat-transfer surfaces. By selectivity is meant the conversion of ethylbenzene to ethylbenzene hydroperoxide, relative to the conversion of ethylbenzene to less desirable materials such as acetophenone, alpha phenyl ethanol, and acids such as benzoic acid. It is a particularly beneficial feature of this invention that a minimum conversion of ethylbenzene to acids is achieved, at any fixed total conversion level of ethylbenzene. Such minimum acid production is highly desirable, both from the standpoint of optimum reaction yield and from the standpoint of minimizing acid-catalyzed side reactions in subsequent processing steps, especially when the ethylbenzene hydroperoxide is to be used as an epoxidizing agent for the conversion of olefins to olefin oxides. The reason for the selectivity enhancement when recycle inert gas is used for temperature control is not fully understood, but it is believed to be the result of the increased evaporation of ethylbenzene from the downstream reaction zones, which at any given overall conversion level results in lower average concentrations of ethylbenzene hydroperoxide and other oxidizable species such as acetophenone and alpha phenyl ethanol along the reaction path. By lowering these concentrations a more favorable oxidation environment is achieved.

In addition to the higher selectivities obtainable, the recycle gas cooling system provides additional advantages through improved control of oxygen partial pressures in gas streams entering and leaving the several reaction zones. Such control is important for maintaining steady reaction rates and safe operation outside flammable gas regions.

In systems for the oxidation of ethylbenzene to ethylbenzene hydroperoxide, and especially in a system involving temperature control by means of inert gas recycle in accordance with this invention, substantial quantities of ethylbenzene vapor are removed from the oxidation zone during the oxidation. It is desirable from the standpoint of greatest process economies that the heat contained in such vapors be efficiently recovered and transferred to other reaction streams. Moreover, in the chemical reaction wherein ethylbenzene hydroperoxide is formed, the conversion of ethylbenzene during the oxidation is necessarily limited in order to avoid excessive decomposition of the desired hydroperoxide product. Low conversions of ethylbenzene, however, require efficient recovery and recycle of unreacted ethylbenzene but such recycled ethylbenzene should be substantially free of contaminating materials, such as water and organic acids, which may tend to interfere with the desired production of ethylbenzene hydroperoxide. It is thus useful to free the recycled ethylbenzene from such contaminants.

Thus, in accordance with a preferred embodiment of the present invention, the above objectives of economy in the recovery of heat from the exiting vapors and recycle of ethylbenzene which is substantially free from water and organic acids are accomplished by the provision of a direct contact between liquid recycle ethylbenzene and vapors exiting from the oxidation reactor. By means of this direct contact, rapid and efficient heat exchange between the vapors and the recycle liquid takes place, thus minimizing the degradation of thermal energy to lower temperatures, and also avoiding the necessity for extensive mechanical surfaces which would be required if the heat were to be recovered through indirect exchange. Additionally, as a result of the contact both water and low boiling organic acids contained in the recycle liquid ethylbenzene are stripped therefrom and the heated liquid ethylbenzene is substantially improved in purity and is highly suited for feeding to the oxidation reaction.

Figure 2:
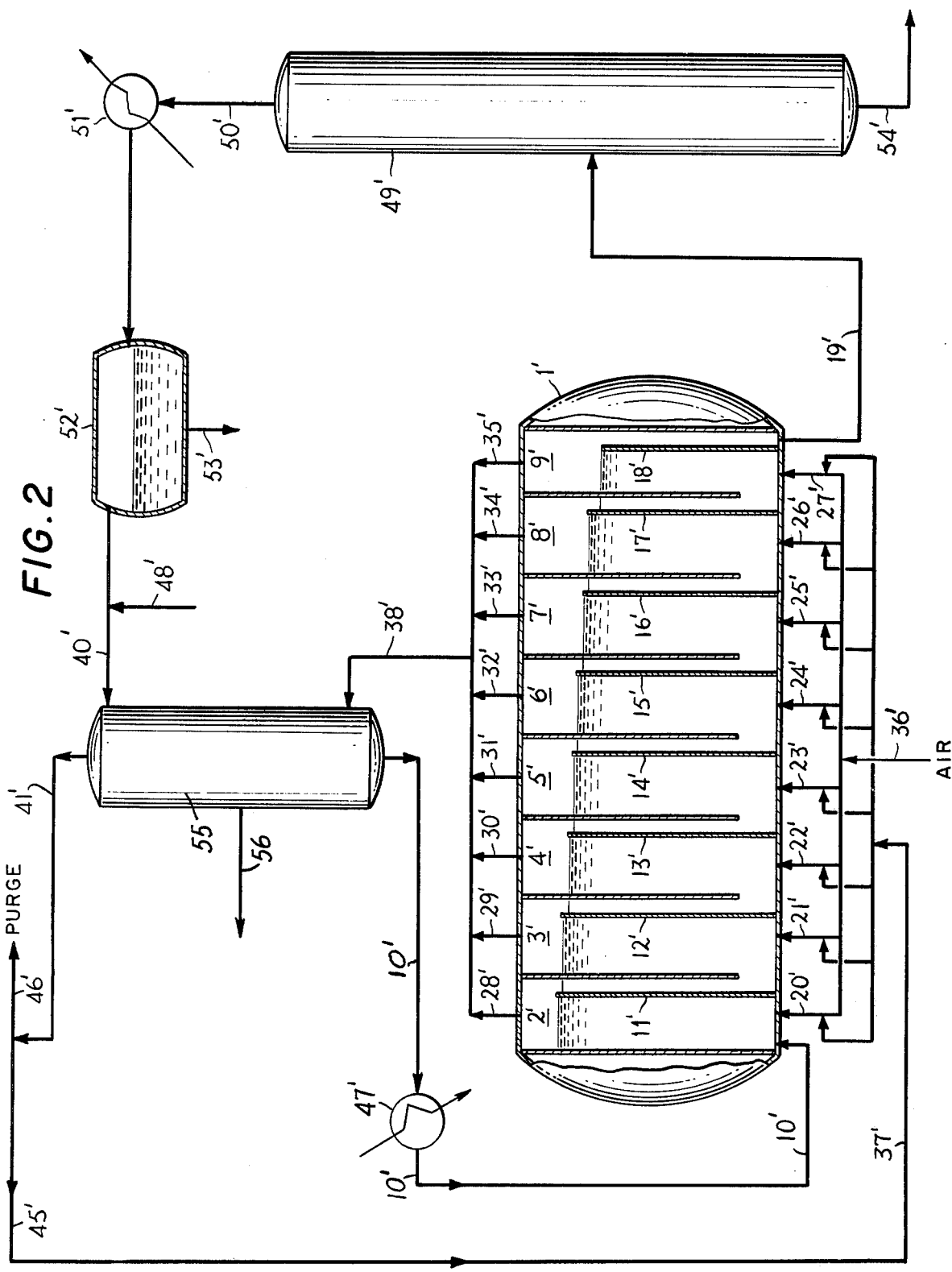

In order more fully to describe the invention, reference is made to the accompanying drawings wherein, FIG. 1 illustrates diagrammatically a typical system for the practice of the process of the present invention, and FIG. 2 is a similar view of a system for carrying out the preferred embodiment of the invention.

It will be understood that the description of the drawings is for purposes of facilitating the understanding of the invention and it is not intended that the invention be limited to process configurations such as shown in these drawings.

Referring to the drawings, and more specifically to FIG. 1, reference numeral 1 designates a cylindrical horizontal reactor which is divided by overflow and baffling means, e.g., weirs, into eight separate oxidation zones numbered consecutively as zones 2, 3, 4, 5, 6, 7, 8, and 9. Ethylbenzene is fed to the first oxidation zone 2 in liquid form via line 10. Liquid from zone 2 overflows weir 11 and passes to zone 3. Liquid from zone 3 overflows weir 12 and passes to zone 4. Liquid from zone 4 overflows weir 13 and passes to zone 5. Liquid from zone 5 overflows weir 14 and passes to zone 6. Similarly, liquid from zone 6 overflows weir 15 and passes to zone 7; liquid from zone 7 overflows weir 16 and passes to zone 8; liquid from zone 8 overflows weir 17 and passes to zone 9. Finally, liquid from zone 9 overflows weir 18 and is withdrawn from reaction 1 by means of line 19.

Vapor inlet means are provided for each of reactor zones 2, 3, 4, 5, 6, 7, 8, and 9. Thus, line 20 provides vapor to zone 2, line 21 provides vapor to zone 3, line 22 provides vapor to zone 4, line 23 provides vapor to zone 5, line 24 provides vapor to zone 6, line 25 provides vapor to zone 7, line 26 provides vapor to zone 8, and line 27 provides vapor to zone 9. Likewise, each of zones 2 through 9 is provided with vapor draw-off lines 28, 29, 30, 31, 32, 33, 34, and 35 for zones 2, 3, 4, 5, 6, 7, 8, and 9, respectively. Air is provided through line 36 to the vapor inlet lines and recycle inert gas is provided through line 37 to each of the vapor inlet lines. Alternatively, the air and recycle gas feeds to any zone may enter the zone through separate lines, if desired. Although not shown, each of the vapor inlet and withdrawal lines is equipped with suitable valves and flow measurement and control means. Liquid ethylbenzene fed to zone 2 is contacted therein at appropriate oxidation temperature with molecular oxygen provided via lines 36 and 20. Flow rates are controlled in order to provide the desired residence time necessary to effect appropriate ethylbenzene oxidation in this zone. Liquid from zone 2 passes continuously to zone 3 wherein additional oxidation takes place through contact with molecular oxygen introduced through lines 36 and 21. Liquid from zone 3 flows continuously to zone 4 where further oxidation takes place by contact with molecular oxygen introduced through lines 36 and 22. Liquid from zone 4 passes continuously to zone 5 where oxidation takes place through contact with molecular oxygen introduced through lines 36 and 23. Liquid from zone 5 passes continuously to zone 6 where oxidation takes place through contact with oxygen introduced through lines 36 and 24. Liquid from zone 6 passes continuously to zone 7 wherein oxidation takes place through contact with oxygen introduced through lines 36 and 25. Liquid from zone 7 passes continuously to zone 8 wherein oxidation takes place through contact with oxygen introduced through lines 36 and 26, and liquid from zone 8 passes to the last oxidation zone 9 wherein final oxidation takes place by contact with molecular oxygen introduced through lines 36 and 27. During the continuous oxidation, vapors are removed from zones 2 through 9 continuously by means of lines 28 through 35 and pass through a common conduit 38. Since the vapor removal lines pass to a common conduit it is apparent that zones 2 through 9 operate at substantially the same pressure.

It is extremely advantageous that the liquid oxidation reaction mixture temperature be highest in zone 2 and steadily decrease so that it is lowest in zone 9. In accordance with the present invention, the temperature control in each of zones 2 through 9 is achieved by appropriate regulation of the amount of recycle inert gas, in this case nitrogen available in the air feed, such that a suitable amount of ethylbenzene is vaporized in each zone to cool incoming reaction liquid to the desired zone temperature and to balance the amount of exothermal heat generated by the oxidation in the particular zone. In other words, inert gas is provided to at least some of the zones, and preferably to each zone, in controlled amounts necessary to attain and maintain the desired temperature in the zones by removing heat through vaporizing ethylbenzene.

As seen in FIG. 1, the vapors removed from the oxidation zones, primarily nitrogen and ethylbenzene, pass via line 38 to a condenser 39. In condenser 39 the vapors are cooled and the condensible components such as ethylbenzene and water are condensed. From condenser 39 the mixture of condensate and gas passes via line 41 to separation zone 42 wherein the condensed material are separated and removed via line 43, the condensed ethylbenzene being subsequently removed and recycled to the system via line 10. The non-condensible inert gases exit via line 44, the needed amount being recycled via lines 45 and 37 for appropriate distribution among the various oxidation zones. An inert gas purge is removed via line 46 in amount necessary to balance the net inert gas entering with the air oxidant. Ethylbenzene introduced via line 40 passes through a preheater 47 and then via line 10 to oxidation zone 2. Net makeup ethylbenzene is added, as shown, via line 48.

For reasons of selectivity it is necessary that the total ethylbenzene conversion in the oxidation zones be fairly low, illustratively not exceeding 25%. Ethylbenzene hydroperoxide tends to decompose at oxidation conditions where present in higher concentrations and thus it is necessary to maintain the ethylbenzene conversion at a fairly low level. The hydroperoxide-containing liquid reaction mixture removed from reactor 1 by means of line 19 illustratively passes to distillation zone 49 wherein unreacted ethylbenzene is distilled overhead, removed via line 50, condensed in condenser 51 and separated from aqueous materials in decantation zone 52. A lower aqueous phase is removed via line 53 and the recycle ethylbenzene is removed via line 40 and passed to the oxidation reaction, as previously discussed. A convenient way to recover the ethylbenzene from separator 42 and return it to the system is to pass the condensate removed via line 43 to decantation zone 52. The concentrated ethylbenzene hydroperoxide stream is removed from zone 49 by means of line 54 and is suitable for a variety of uses, most desirably for use in the epoxidation of olefins by procedures fully described, for example, in U.S. Pat. Nos. 3,351,635, 3,459,810 and 3,475,498.

Referring now to FIG. 2, it will be seen that parts corresponding to those shown in FIG. 1 are given the same reference numeral to which a prime has been added. Thus, in the embodiment of FIG. 2, the vapors removed from the oxidation zones, primarily nitrogen and ethylbenzene, pass via line 38' to a contact column 55 wherein the vapors are cooled and substantial quantities of ethylbenzene vapor are condensed. The non-condensible inert gases containing some residual ethylbenzene vapor exit via line 41', the needed amount being recycled via lines 45' and 37' for appropriate distribution among the various oxidation zones. An inert gas purge is removed via line 46' in amount necessary to balance the net inert gas entering with the air oxidant. Heated ethylbenzene from contact zone 55 passes via line 10' to preheater 47', which is optionally used in this embodiment, and thence via line 10' to oxidation zone 2'. Net makeup ethylbenzene is added, as shown, via line 48'. Contact column 55 is suitably provided with internal or external decantation means for removing impurities such as water and organic acids. For example, contact column 55 may be provided with a well-known "chimney tray" which functions as a decanter to separate the condensed aqueous phase from the ethylbenzene, the aqueous phase being withdrawn through line 56. Alternatively, the aqueous phase may be separated from the ethylbenzene in a decanter (not shown) external to the contact column.

By way of a general description of appropriate oxidation reaction conditions it is ordinarily advantageous that the ethylbenzene oxidation be carried out at temperatures ranging from about 100° to about 165° C. A preferred temperature range is 130° to 160° C, with temperatures ranging from 135° to 160° C. being most preferred. System pressure during the oxidation ranges from about 1 to about 1000 p.s.i.g. although pressures outside this range can be used.

It is generally advantageous to oxidize 5 to about 20% of the ethylbenzene, since below about 5% conversion the cost of separating and recycling ethylbenzene becomes prohibitive. At conversions above 20% or so selectivity decreases through decomposition of the ethylbenzene hydroperoxide. Preferred conversions of ethylbenzene, as reflected by the molar concentration of oxidation products in the liquid effluent from the last oxidation zone are about 7 to 12%. It is not necessary to employ catalysts or other additives during the oxidation although stabilizers, initiators and the like as known in the art can, if desired, be employed.

It will be apparent to those skilled in the art that many different embodiments of the present invention are possible. For example, in the attached drawing the oxidation reactor is depicted as a single cylindrical reactor divided into different separate sections or reaction zones. Obviously, an alternative embodiment would involve the use of individual and separate reactors in series connected by appropriate conduits. Each zone is provided with suitable agitation means (not shown) which may be of any desired type, including agitation by the gases alone or by mechanical methods. Likewise, other heat-exchange means for recovering heat from the vapors removed from the oxidation zones are possible and, of course, different distillation procedures for separating product are feasible. As previously mentioned, the inert gas recycle process of the invention is not limited to a system in which there is counter-current contact between the gases from the reactor and the incoming ethylbenzene as shown in FIG. 2. The inert gases, after condensible components have been separated by any suitable means, can be directly recycled to the oxidation zones, as shown in FIG. 1 although, as discussed above, the process of this invention is particularly suitable for use with a system which involves such contact between reaction gases and recycle ethylbenzene. It might be noted that usually the hydroperoxide is not separated from all of the ethylbenzene before use. Accordingly, after the hydroperoxide has been reacted, for example, in an epoxidation, separation procedures are generally provided for recovery of the remainder of the unreacted ethylbenzene which can be recycled to the oxidation zone as part of the feed liquid ethylbenzene by means which are not shown in the attached drawings.

As previously mentioned, the accompanying drawings are merely diagrammatic and it will be understood that, in carrying out the process of the present invention conventional equipment accessories of auxiliary units, which have not been illustrated in order to simplify the drawings, may normally be employed as will be well understood by persons skilled in the art. Thus, compressors (not illustrated) can be employed to provide vapor streams at desired pressures. Similarly, as previously mentioned, the various lines through which vapor or liquid streams will flow are suitably provided with appropriate valves and may be provided with heating or cooling means (not illustrated) to regulate the temperatures of the streams, when desired.

The following examples illustrate appropriate specific practices of the present invention, but it is to be understood that these examples are given for illustrative purposes only and are not to be interpreted as limitative of the invention.

EXAMPLE 1

Ethylbenzene is oxidized with molecular oxygen to ethylbenzene hydroperoxide using the recycle gas system of the invention as illustrated schematically in FIG. 1. The vapors in line 38 are passed to condenser 39 and thence to separator 42. Aqueous condensate is purged from this separator, and condensed ethylbenzene separated from the aqueous phase is returned to oxidation via line 10. Uncondensed vapors from the separator via line 44 are recycled via lines 45 and 37 to the reaction zone in order to provide the required temperature control, sufficient purge of non-condensibles being taken via line 46 to compensate for these materials entering with the incoming air via line 36. The oxidation is carried out in a continuous manner employing eight oxidation zones 2 through 9 as shown in the drawing. The liquid-phase oxidation mixture in zone 2 is maintained at 146° C, that in zone 3 at 144° C, that in zone 4 at 142° C, that in zone 5 at 140° C, that in zone 6 at 138° C, that in zone 7 at 136° C, that in zone 8 at 134° C and that in zone 9 at 132° C. The vapor withdrawal lines from each zone are connected to common conduit 38 and the pressure in each of the oxidation zones is maintained at about 33 p.s.i.a.

Ethylbenzene heated to about 148° C in preheater 47 is fed by means of line 10 to oxidation zone 2 at a rate of about 234 mols/hr. Air, which has been preheated to about 130° C, is fed to reactor 1 at the rate of about 79.4 mols/hr. via line 36 and is distributed to the several oxidation zones 2–9 as hereinafter described. The vapors from the oxidation zones leave through line 38 at the rate of about 192 mols/hr. and have a molar composition of about 54% nitrogen, 44% ethylbenzene, and 1% oxygen, the remainder including water and organic byproducts. After cooling of these vapors to recover condensibles and separation of the uncondensed vapors and after removal of the above-mentioned purge, the resulting recycle gas is compressed (by means not shown) and is passed to reactor 1 at the rate of about 41.7 mols/hr. via line 37 and is distributed to the eight oxidation zones as hereinafter described. The molar composition of this recycle gas is about 97% nitrogen, 2% oxygen, and 1% ethylbenzene. The condensed ethylbenzene removed from the separator 42 via line 43, is sent to line 40 for recycle.

The liquid effluent from the last oxidation zone (9) contains approximately 9.5 mol % (12 weight %) ethylbenzene hydroperoxide and 89 mol % ethylbenzene, the remainder being organic byproducts. This mixture is distilled at a pot temperature of about 80° C and approximately 50% of the contained ethylbenzene is removed and recycled to the oxidation. The remainder of the ethylbenzene is recovered in subsequent processing for recycle to the oxidation. The following table shows the manner in which air and recycled inert gas are distributed (expressed as mols per hour) among the eight oxidation zones. The recycled gas is calculated on an ethylbenzene-free basis.

|        | Air  | Recycled Gas |
|--------|------|--------------|
| Zone 2 | 7.8  | 0            |
| Zone 3 | 9.8  | 0            |
| Zone 4 | 10.7 | 1.2          |
| Zone 5 | 11.0 | 3.2          |
| Zone 6 | 10.9 | 5.2          |
| Zone 7 | 10.4 | 7.8          |
| Zone 8 | 9.8  | 10.7         |
| Zone 9 | 9.0  | 13.8         |

The above-described process produces 88 mols of ethylbenzene hydroperoxide per 100 mols of ethylbenzene oxidized, and 6.7 mols of acetophenone byproduct per 100 mols of ethylbenzene hydroperoxide.

EXAMPLE 2

Ethylbenzene is oxidized with molecular oxygen to ethylbenzene hydroperoxide but without the recycle gas system of the invention described in Example 1 and illustrated in FIG. 1, the vapors passing from line 38 to condenser 39 and thence to separator 42. Aqueous condensate and noncondensibles are purged from this separator, and condensed ethylbenzene is returned from the separator to oxidation via line 10. The oxidation is carried out in a continuous manner employing eight oxidation zones 2 through 9 as shown in the drawing. The liquid-phase oxidation mixture in zone 2 is maintained at 146° C, that in zone 3 at 144° C, that in zone 4 at 142° C, that in zone 5 at 140° C, that in zone 6 at 138° C, that in zone 7 at 136° C, that in zone 8 at 134° C, and that in zone 9 at 132° C. Temperature control is accomplished by cooling coils (not shown) provided in each compartment. The vapor withdrawal lines from each zone are connected to common conduit 38 and the pressure in each of the oxidation zones is maintained at about 33 p.s.i.a.

Ethylbenzene heated to about 148° C in preheater 47 is fed by means of line 10 to oxidation zone 2 at a rate of about 205 mols/hr. Air, which has been preheated by means not shown to about 130° C, is fed to reactor 1 at the rate of about 81.5 mols/hr. via line 36 and is distributed to the several oxidation zones 2–9 as hereinafter described. The combined vapors from the oxidation zones leave through line 38 at the rate of about 124 mols/hr., and have a molar composition of about 52% nitrogen, 46% ethylbenzene, and 1% oxygen, the remainder including water and organic byproducts. The vapors are cooled to recover condensibles, as previously noted. The following table shows the manner in which air is distributed among the eight oxidation zones.

|        | Air (Mols per hour) |
|--------|---------------------|
| Zone 2 | 8.1                 |
| Zone 3 | 10.2                |
| Zone 4 | 11.1                |
| Zone 5 | 11.3                |
| Zone 6 | 11.1                |
| Zone 7 | 10.6                |
| Zone 8 | 9.9                 |
| Zone 9 | 9.2                 |

The liquid effluent from the last oxidation zone (9) contains approximately 9.5 mol % (12 weight %) ethylbenzene hydroperoxide, and 89 mol % ethylbenzene, the remainder being organic byproducts. This mixture is distilled at a pot temperature of about 80° C and approximately 50% of the contained ethylbenzene is removed and recycled to the oxidation. The remainder of the ethylbenzene is recovered in subsequent processing for recycle to the oxidation.

The foregoing process produces only 86 mols of ethylbenzene hydroperoxide per 100 mols of ethylbenzene oxidized, and produces 8.0 mols of acetophenone byproduct per 100 mols of ethylbenzene hydroperoxide.

EXAMPLE 3

The process of Example 1 is repeated using the recycle of inert gas to the oxidation zones in accordance with the invention as described above, but in this case the system of FIG. 2 is employed so that there is direct contact of feed ethylbenzene with the oxidation vapors. Thus, the feed ethylbenzene from line 40' is passed to the upper portion of contact zone 55 and the oxidation vapors in line 38' pass into the lower portion of contact zone 55 for countercurrent contact with the ethylbenzene. The condensed and decanted water phase is removed via line 56, the cooled gases are removed through line 41' for recycle to the oxidation after appropriate purge, and the heated ethylbenzene enters line 10' and passes to oxidation zone 2' after passing through preheater 47'. The conditions of operation correspond to those described in Example 1. When operating in this manner, substantially the same results in terms of ethylbenzene hydroperoxide and byproduct production are realized, but there are important improvements in process efficiencies and economies. Thus, the process of this example requires a heat input to preheater 47' of only about 18,000 calories per gram mol of ethylbenzene hydroperoxide produced compared with a corresponding heat input to preheater 47 of about 108,000 calories per gram mol for the process of Example 1.

What is claimed is:

1. A process for the preparation of ethylbenzene hydroperoxide by the liquid-phase molecular oxygen oxidation of ethylbenzene in a reaction zone wherein liquid flows from an upstream portion to a downstream portion of said reaction zone which comprises the steps of introducing liquid ethylbenzene into the upstream portion of said reaction zone, introducing air into said reaction zone for direct contact of said molecular oxygen with said ethylbenzene in said zone, removing vapors comprising non-condensible inert gases from said reaction zone, cooling said vapors to separate condensible components from said vapors, recycling said cooled non-condensible gases to said reaction zone, and removing a liquid stream containing product ethylbenzene hydroperoxide from the downstream portion of said reaction zone, said zone being under a pressure of about 1 psig to about 1000 psig and said cooled recycling noncondensible gases being introduced into said zone at a rate to control the temperature of said zone within the range of about 100° to about 165° C., said temperature decreasing from the upstream portion of said zone to the downstream portion of said zone.

2. A process as defined in claim 1, wherein said reaction zone is divided into a plurality of oxidation zones interconnected in series, said ethylbenzene being introduced into the first of said oxidation zones, said vapors being removed from all of said oxidation zones, said recycling non-condensible inert gases and said air being introduced into at least a portion of said oxidation zones and said liquid stream containing product ethylbenzene hydroperoxide being removed from the last of said oxidation zones.

3. A process as defined in claim 1, wherein said liquid stream is treated to separate at least some of the unreacted ethylbenzene therefrom and said thus-separated ethylbenzene is recycled to said reaction zone.

4. A process as defined in claim 1, wherein said liquid ethylbenzene introduced into said reaction zone is first brought into contact with said vapors removed from said reaction zone.

5. A process as defined in claim 2, wherein said liquid ethylbenzene introduced into said reaction zone is first brought into contact with said vapors removed from said reaction zone.

* * * * *